(12) United States Patent
Jones et al.

(10) Patent No.: US 6,506,156 B1
(45) Date of Patent: Jan. 14, 2003

(54) ECHOGENIC COATING

(75) Inventors: Michael L. Jones, Capistrano Beach, CA (US); Jill Uyeno, Mission Viejo, CA (US); Greig E. Altieri, Laguna Beach, CA (US)

(73) Assignee: Vascular Control Systems, Inc, San Juan Capistrano, CA (US)

(*) Notice: Subject to any disclaimer, the term of this patent is extended or adjusted under 35 U.S.C. 154(b) by 0 days.

(21) Appl. No.: 09/488,467

(22) Filed: Jan. 19, 2000

(51) Int. Cl.[7] .................................................. A61B 8/00
(52) U.S. Cl. ........................................ 600/439; 600/432
(58) Field of Search ................................ 600/447, 437, 600/439, 462, 459, 460, 458, 449; 607/122

(56) References Cited

U.S. PATENT DOCUMENTS

| | | |
|---|---|---|
| 4,428,379 A | 1/1984 | Robbins et al. |
| 5,081,997 A | 1/1992 | Bosley, Jr. et al. |
| 5,201,314 A | 4/1993 | Bosley et al. |
| 5,289,831 A | 3/1994 | Bosley |
| 5,383,922 A | 1/1995 | Zipes et al. |
| 5,716,389 A | 2/1998 | Walinsky et al. |
| 5,720,743 A | 2/1998 | Bischof et al. |
| 5,759,154 A | 6/1998 | Hoyns |
| 5,766,135 A | 6/1998 | Terwilliger |
| 5,769,795 A | 6/1998 | Terwilliger |
| 5,797,397 A | 8/1998 | Rosenberg |
| 5,800,378 A | 9/1998 | Edwards et al. |
| 5,817,022 A | 10/1998 | Vesely |
| 5,836,906 A | 11/1998 | Edwards |
| 5,840,033 A | 11/1998 | Takeuchi |
| 5,895,386 A | 4/1999 | Odell et al. |
| 5,899,861 A | 5/1999 | Friemel et al. |
| 5,911,691 A | 6/1999 | Mochizuki et al. |
| 5,921,933 A * | 7/1999 | Sarkis et al. ............... 600/459 |
| 5,941,889 A | 8/1999 | Cermak |
| 6,045,508 A * | 4/2000 | Hossack et al. ............ 600/447 |
| 6,106,473 A * | 8/2000 | Violante et al. ............ 600/458 |
| 6,231,515 B1 * | 5/2001 | Moore et al. ............... 600/466 |

FOREIGN PATENT DOCUMENTS

WO      WO98/19713      5/1998

* cited by examiner

Primary Examiner—Marvin M. Lateef
Assistant Examiner—Maulin Patel
(74) Attorney, Agent, or Firm—Coudert Brothers LLP

(57) ABSTRACT

Medical devices that are coated with an echogenic material that includes an electrically insulative base layer and an echogenic layer demonstrate both improved ultrasonic imaging and protection against RF electrical breakdown. The echogenic layer includes a polymeric matrix that (i) defines a plurality of void spaces, (ii) includes glass microsphere particles, or (iii) both defines a plurality of void spaces and includes glass microsphere particles. Medical instruments exhibit enhanced ultrasonic imaging even when viewed along their lengths.

32 Claims, 6 Drawing Sheets

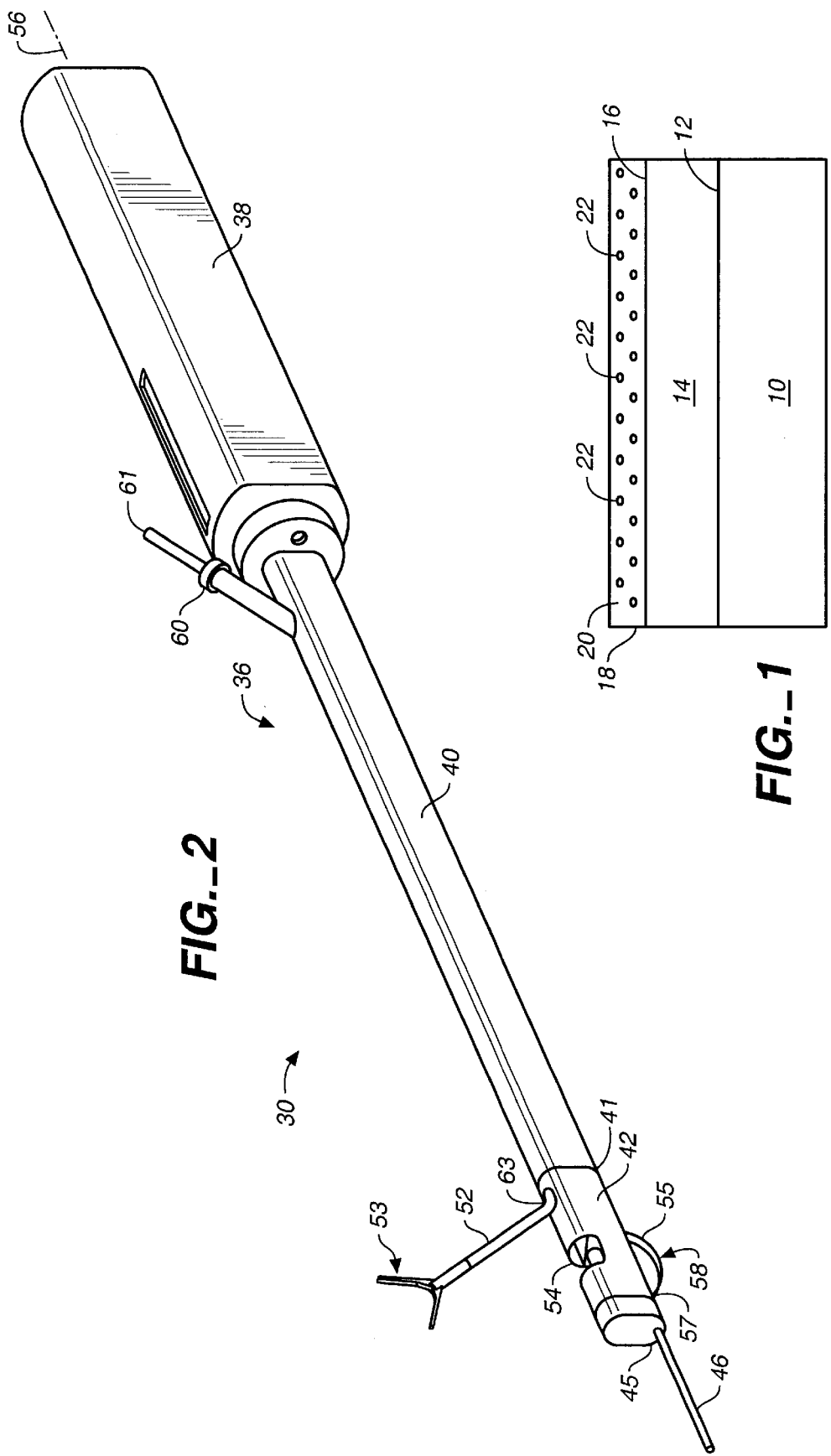

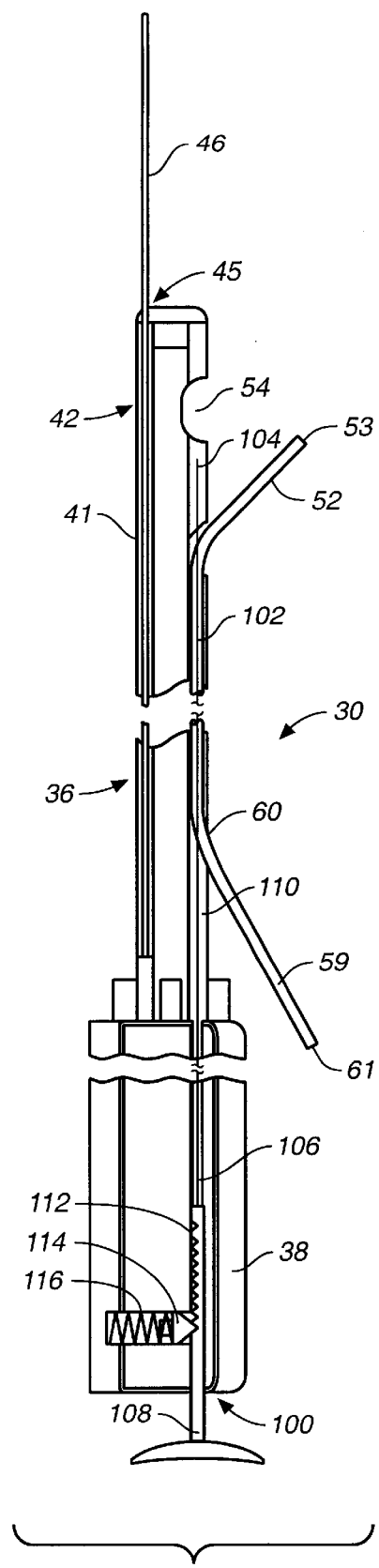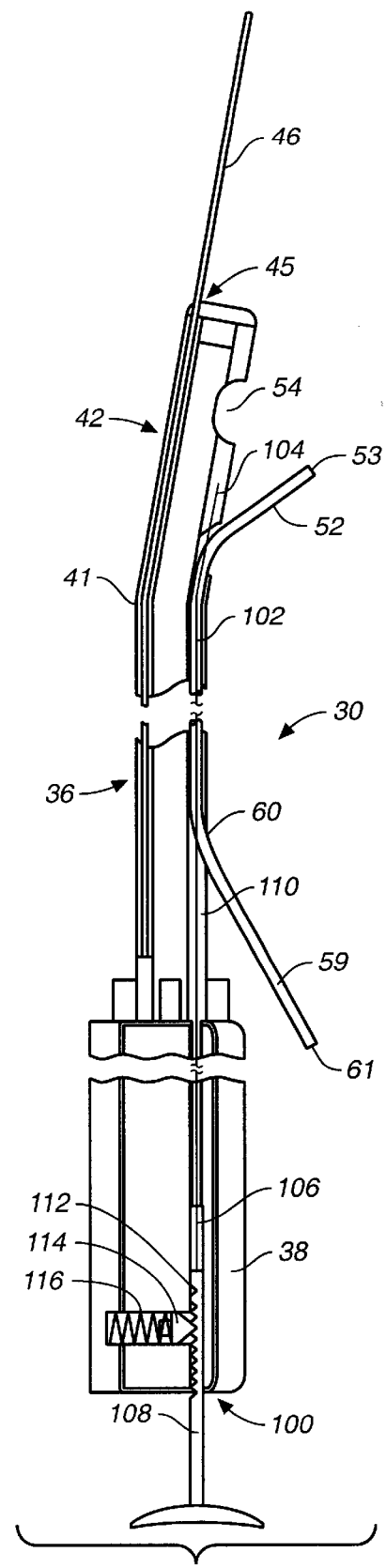
FIG._3    FIG._4

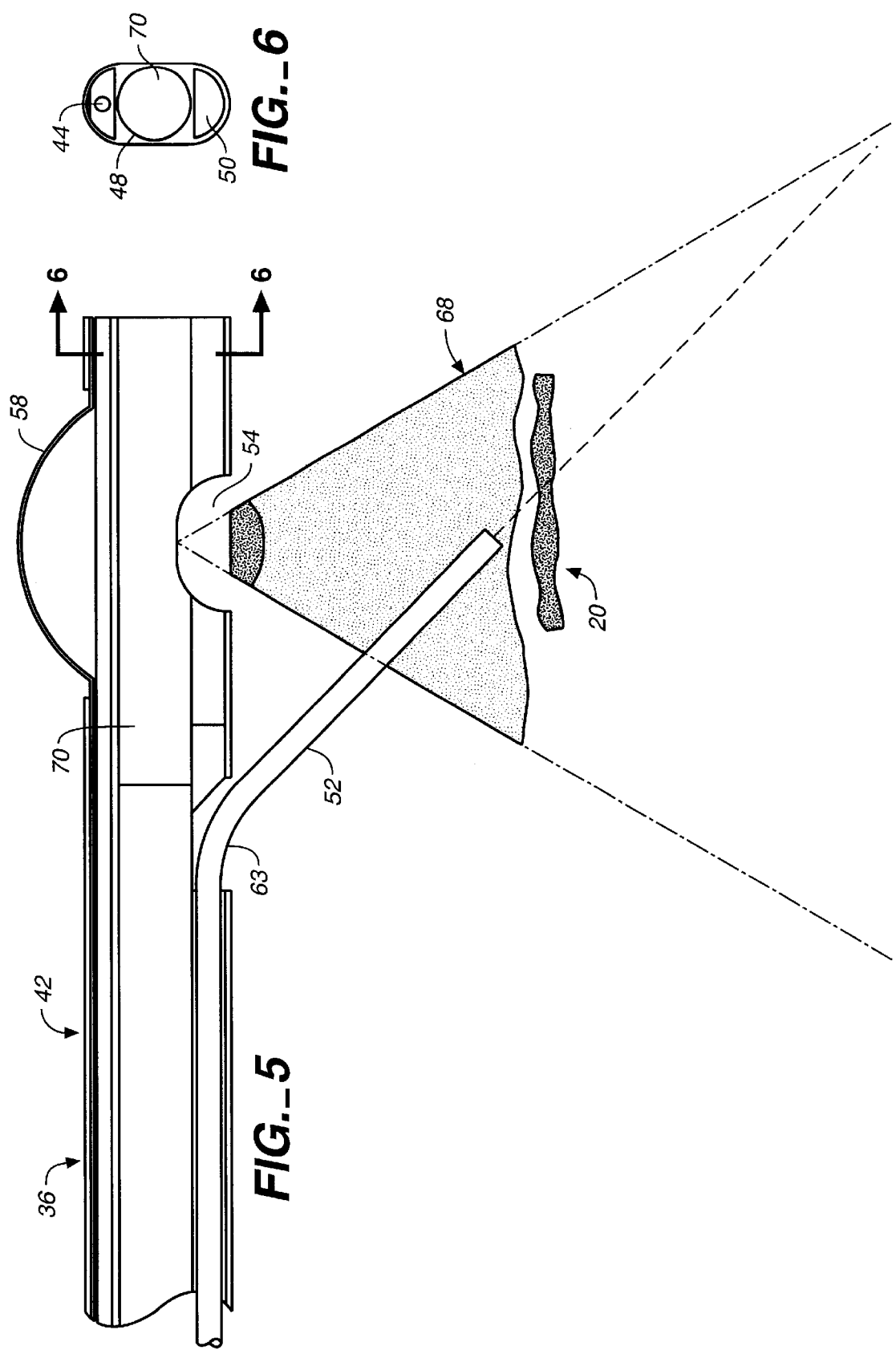

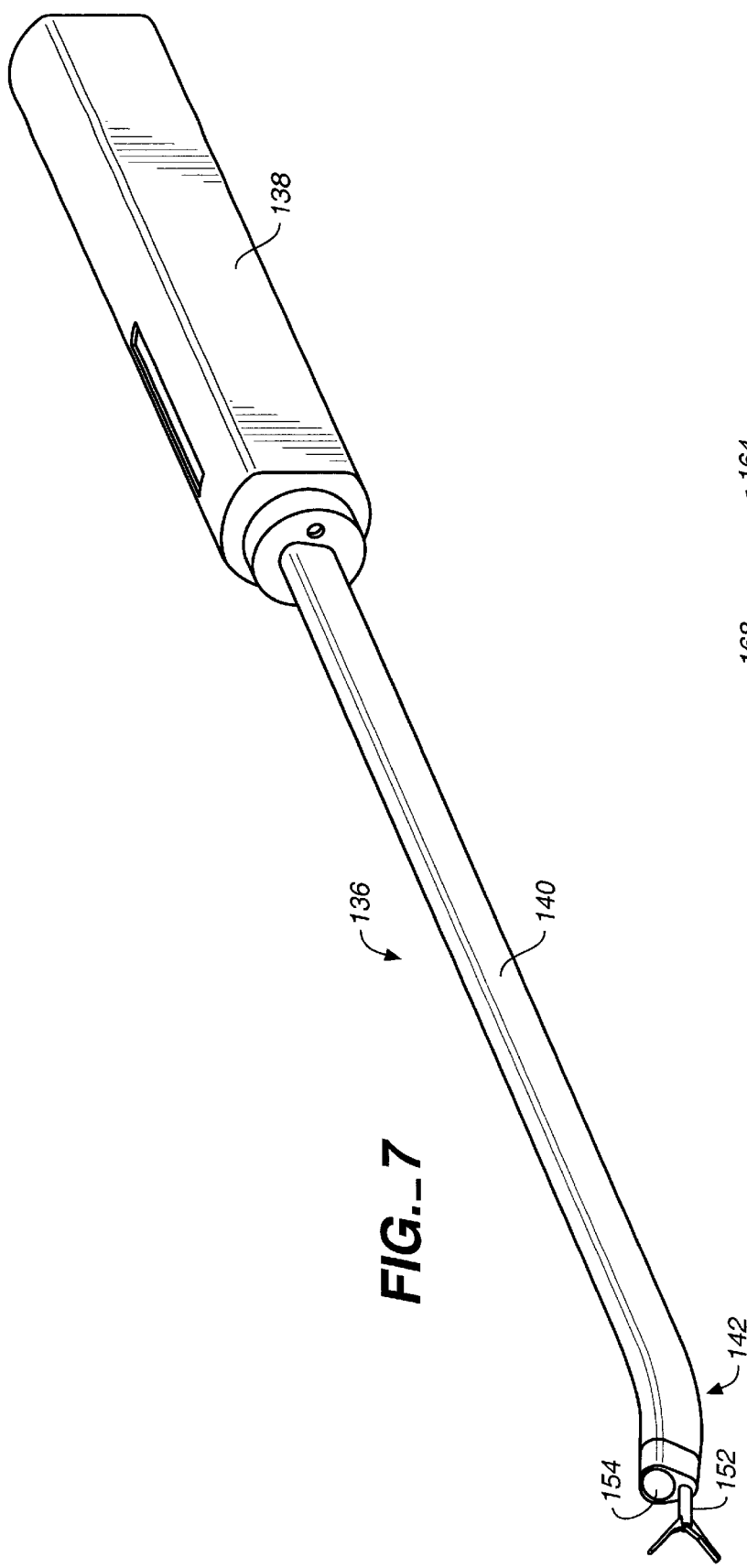
FIG._7
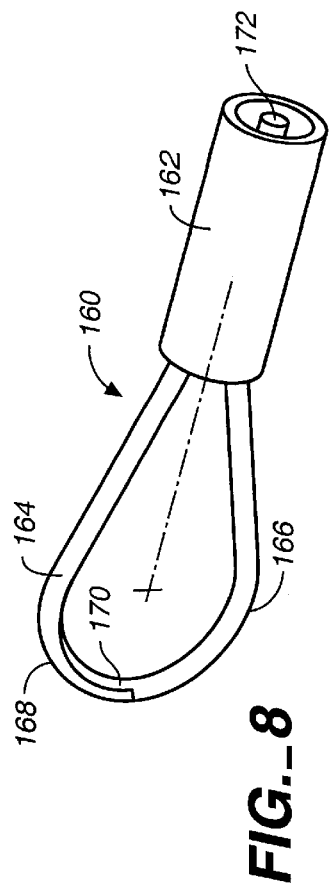
FIG._8

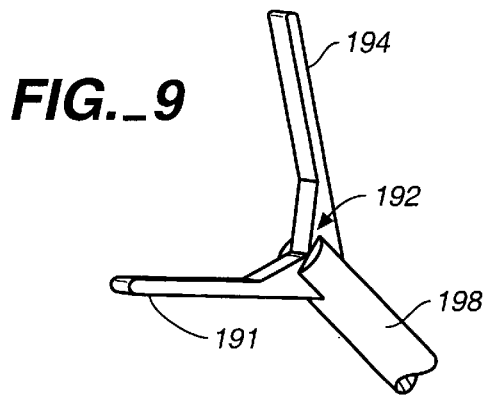
FIG._9
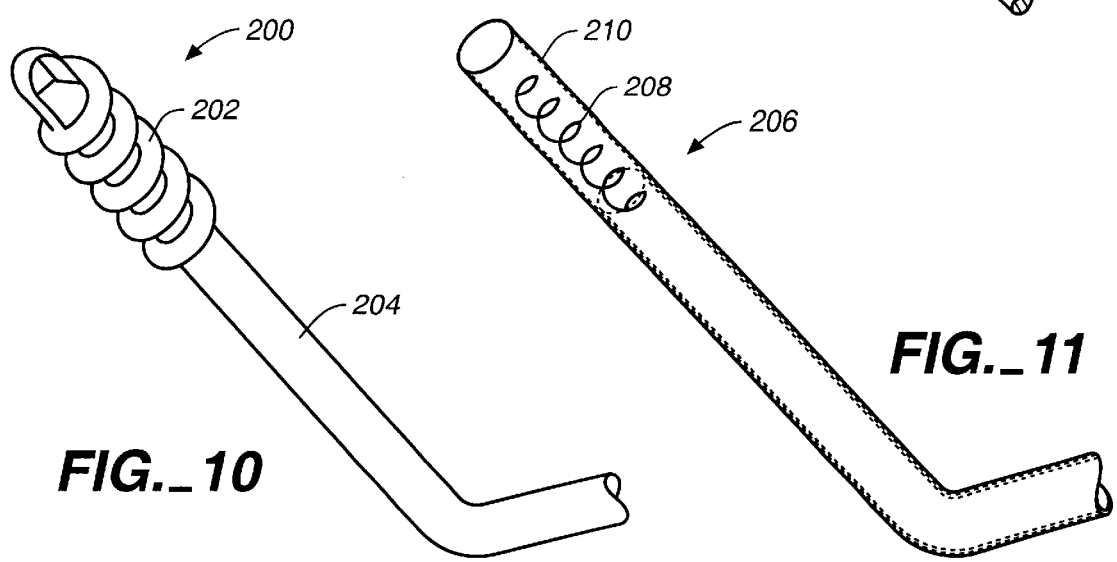
FIG._10
FIG._11
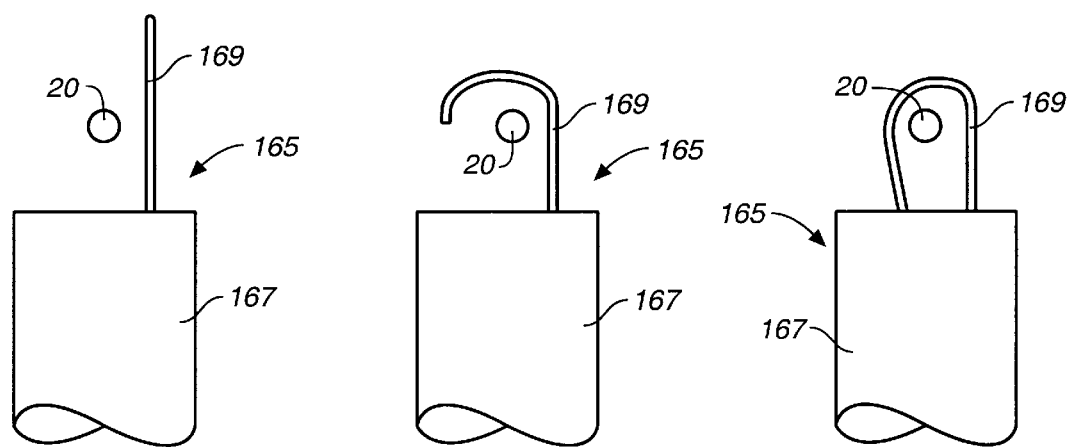
FIG._11a   FIG._11b   FIG._11c

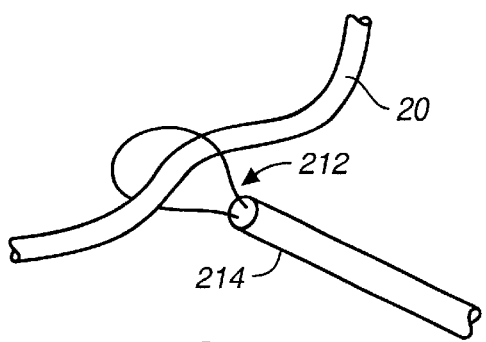
FIG._12
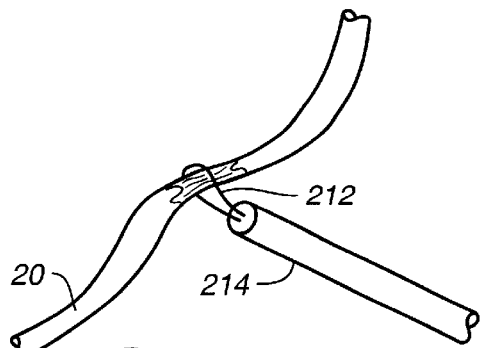
FIG._13
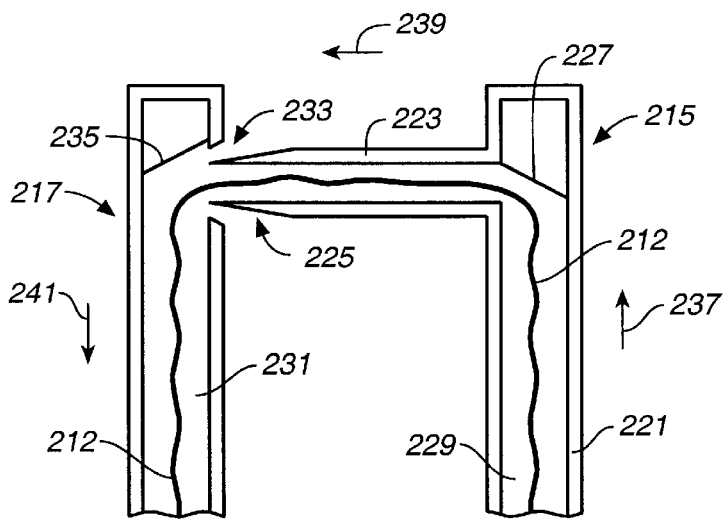
FIG._12a
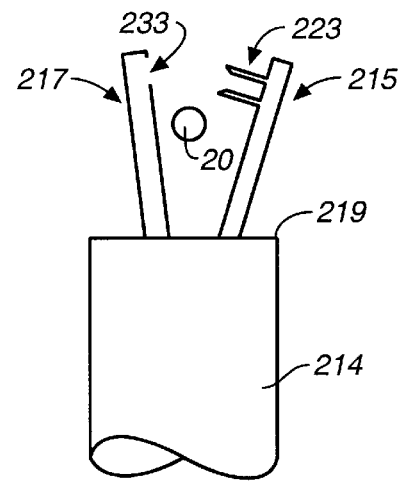
FIG._12b
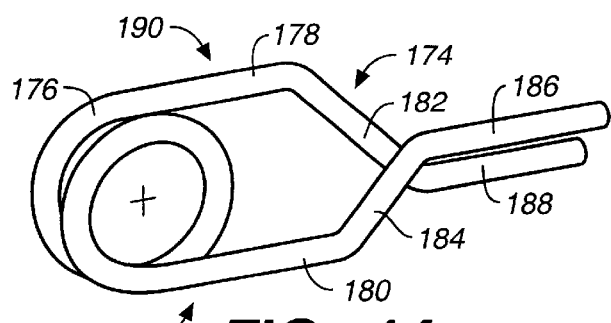
FIG._14

ECHOGENIC COATING

FIELD OF THE INVENTION

This invention relates to echogenic coatings for medical devices used with ultrasound imaging systems and, more particularly, to echogenic coatings that also afford electrical insulative protection.

BACKGROUND OF THE INVENTION

Ultrasound imaging is widely used in medical applications to noninvasively observe structures within the human body, such as, for example, cardiac structures, the vascular system, the fetus, the uterus, the abdominal organs and the eye. In addition to imaging physiological structures and tissue, ultrasound imaging has also been employed to image medical devices that are inserted into tissue or passageways of the patient. In a typical imaging system, short bursts of ultrasound energy are directed into a patient's body with a transducer. The returning reflected ultrasound energy, or echoes, are received by the same transducer and are converted to electrical signals. The signals representing the reflected energy are processed and formatted into a video image of a target region.

A variety of approaches have been used to enhance ultrasonic images. For example, U.S. Pat. No. 5,201,314 describes a medical device that is insertable into tissue or a passageway and imageable with sonic imaging equipment. The device includes an elongated insertable member that has an interface having a shape that is responsive to the sonic beam for producing the image. The elongated member includes a substance such as spherically or other geometrically-shaped particles that have a predetermined contour for establishing the interface. This contoured substance is contained within the material of the elongated member or alternatively or in combination attached to or embedded in the outside surface of the member material. In one case, the member material comprises a plastic for surrounding spherically-shaped glass particles, which may consist of a high density metal such as barium or tungsten or a glass material.

U.S. Pat. No. 5,921,933 describes medical devices that are employed within the human body and which purportedly have enhanced ultrasound visibility by virtue of incorporation of an echogenic material on the device surface. The material is fabricated by incorporating particles of sonically reflective materials, for example, iron oxide, titanium oxide or zinc oxide into a biocompatible plastic. The echogenic material can be fabricated by mixing the reflective particles with a powdered thermoplastic or thermosetting material such as a polyether amide, a polyurethane or an epoxy, or polyvinylchloride followed by thermal processing of the mixture to provide a material of increased sonic reflectance which may be applied as a coating on the devices.

U.S. Pat. No. 5,081,997 describes medical devices that include an echogenic body member that is at least partially made up of a composite material which is echogenically imageable in the patient. The composite material includes a plastic matrix material with discrete sound reflective particle embedded therein. Examples of suitable plastics include urethane, silicone, polyethylene, polytetrafluorethylene. The reflective particles are made of a hard material, such as glass particles.

While prior art medical devices having echogenic materials coated thereon can improved ultrasonic imaging, conventional echogenic materials are not suitable for use with medical devices that are exposed to high voltage electrical energy, e.g., radio frequency (RF) energy. The art is in search of echogenic materials that also afford adequate electrical insulation.

SUMMARY OF THE INVENTION

The present invention is based in part on the discovery that metal substrates that are coated with an echogenic material comprising an electrically insulative base layer and an echogenic layer demonstrate both improved ultrasonic imaging and protection against RF electrical breakdown. The echogenic material is particularly suited for coating a medical device component which is viewed along its length.

In one aspect, the invention is directed to an echogenic material that includes:

an electrically insulative base layer and an echogenic layer that comprises a polymeric matrix that (i) defines a plurality of void spaces, (ii) includes glass microsphere particles, or (iii) both defines a plurality of void spaces and includes glass microsphere particles, wherein the echogenic layer is formed on the base layer.

In another aspect, the invention is directed to a process for forming an echogenic layer on a substrate surface that includes the steps of:

(a) applying an electrically insulative base layer on the substrate surface; and (b) creating an echogenic layer on the insulative base layer wherein the echogenic layer comprises a polymeric matrix that (i) defines a plurality of void spaces, (ii) includes glass microsphere particles, or (iii) both defines a plurality of void spaces and includes glass microsphere particles, wherein the echogenic layer is formed on the base layer.

Preferred techniques for fabricating the echogenic layer are electrostatic spraying and fluidized bed coating.

In a further aspect, the invention is directed to a system for applying RF energy to tissue that includes:

an ultrasonic transducer means for sensing a location in the tissue to be treated; and means for applying RF energy that includes an RF probe having a distal end and an RF electrode mounted on the RF probe distal end wherein the RF probe has a surface that has an echogenic material coated thereon which comprises an electrically insulative base layer and an echogenic layer.

Preferably, the echogenic layer includes a polymeric matrix that (i) defines a plurality of void spaces, (ii) includes glass microsphere particles, or (iii) both defines a plurality of void spaces and includes glass microsphere particles.

In yet another aspect, the invention is directed to a medical device for insertion into biological tissue having an echogenic portion of enhanced visibility in an ultrasound scan, wherein the echogenic portion includes a coating comprising an echogenic layer and an electrically insulative layer.

In still another aspect, the invention is directed to a medical device for insertion into biological tissue having a shaft member and a source of RF energy wherein the shaft member has an outer surface that is coated with a coating that includes an echogenic layer and an electrically insulative layer.

In another further aspect, the invention is directed to a method for sonically imaging an echogenic medical device in biological tissue, that includes:

selecting a medical device that includes:

(i) an ultrasonic transducer means for sensing a location in the tissue to be treated; and (ii) means for applying RF energy that includes a shaft member having a distal end and an RF electrode mounted on the shaft member distal end wherein the shaft member has an echogenic material coated thereon which comprises an electrically insulative base layer and an echogenic layer;

inserting the shaft member into the tissue;

directing a sonic beam towards the shaft member;

receiving an image of the shaft member;

maneuvering the RF electrode to the location in the tissue to be treated; and applying RF energy to the tissue.

In another further aspect, the invention is directed to a method for manufacturing an echogenic medical device for insertion into biological tissue and imageable with sonic imaging equipment, that includes:

providing a medical device that includes means for applying RF energy that includes a shaft member having a distal end and an RF electrode mounted on the shaft member distal end; and applying an echogenic coating on the shaft member wherein the echogenic coating comprises an electrically insulative base layer and an echogenic layer.

BRIEF DESCRIPTION OF THE DRAWINGS

FIG. 1 illustrates a substrate that is coated with an electrically insulative layer and an echogenic layer;

FIG. 2 is a perspective illustration of a first exemplary embodiment of an apparatus in accordance with the present invention;

FIGS. 3 and 4 are perspective illustrations of a second exemplary embodiment of an apparatus in accordance with the present invention;

FIG. 5 is a schematic illustration of a distal end portion of an apparatus in accordance with the present invention, and illustrating an imaging plane;

FIG. 6 is a cross-sectional view of the embodiment illustrated in FIG. 5, taken at line 6—6;

FIG. 7 is a schematic illustration of an endviewing embodiment of an apparatus in accordance with the present invention; and FIGS. 8–14 schematically illustrate several additional exemplary embodiments of apparatus in accordance with the present invention;

DESCRIPTION OF THE PREFERRED EMBODIMENT

FIG. 1 illustrates a substrate that is coated with the inventive echogenic and electrically insulative materials. Specifically, the coated substrate 10 includes a layer of insulative material 14 deposited on substrate surface 12 and a layer of echogenic material 18 deposited on insulative material surface 16. The substrate comprises any suitable material that requires electrical insulation. Preferred materials include, for example, (1) metals such as stainless steel and titanium, and (2) other conductive materials.

The echogenic and electrically insulative materials are particularly suited for coating articles that are exposed to electromagnetic radiation (e.g., RF energy) and the like and that are employed in ultrasound for visual analysis. The materials are suited for coating medical devices such as, for example, catheters, stents, cannulae, and the like. As further described herein, the materials are particularly suited for coating devices for causing at least partial occlusions of uterine arteries.

The electrically insulative material preferably comprises (1) thermoset materials such as, for example, epoxies or (2) thermoplastics such as, for example, polyester, polyolefin, polyethylene, polyamide, and fluoropolymers, e.g., polytetrafluoroethylene. A particularly preferred material is NYLON 11 which is easier to apply than polyester and which is able to build a more consistent wall thickness than can polyolefins.

The thickness of the electrically insulative material 14 will vary depending on the particular material used and other parameters such as the geometry and/or dimensions of the substrate surface. Preferably the thickness of the material will be sufficient to pass the breakdown voltage test in accordance with ANSI HF-18. In the case of NYLON 11 coatings, a thickness of 0.0065 in. (165 $\mu$m) should pass this breakdown voltage test. Typically, the electrically insulative layer will have a thickness that ranges from 100 $\mu$m to 300 $\mu$m and preferably from 150 $\mu$m to 200 $\mu$m.

The echogenic layer 18 preferably comprises a polymeric matrix 20 that is enhanced to exhibit echogenic properties. The polymeric matrix comprises a matrix material that can be the same as that which forms the electrically insulative layer. In addition, the echogenic layer further includes (1) particles, (2) voids, or (3) both particles and voids which are represented by reference number 22. The particles and/or voids are preferably evenly distributed throughout the polymeric matrix. The presence of the particles and/or voids imparts improved the ultrasound reflective properties to the echogenic layer. The particles are preferably made of a hard material; it has been found that small glass particles are especially well suited for enhancing ultrasonic images. Specifically, glass particles in the form of microspheres are particularly effective. The outer diameter of the microspheres typically ranges from about 10 $\mu$m to 100 $\mu$m.

When the echogenic layer contains microspheres, preferably they collectively occupy about 10% to 50% by volume of the echogenic layer. The size and geometry of the microspheres can vary; each microsphere will typically have diameters of about 10 $\mu$m to 100 $\mu$m. Similarly, when the echogenic layer contains voids, preferably these void spaces collectively occupy about 10% to 50% by volume of the echogenic layer. The size and geometry of the void spaces can vary and each void space will typically have volumes of about 500 $\mu m^3$ to $6\times10^5$ $\mu m^3$.

The thickness of the echogenic layer will vary depending on the particular polymeric material of the coating, the number of particles and/or voids present, and other parameters such as the geometry and/or dimensions of the surface of the substrate. Typically, the echogenic layer will have a thickness that ranges from 20 $\mu$m to 200 $\mu$m and preferably from 50 $\mu$m to 150 $\mu$m.

Conventional extrusion coating methods can be employed to form either layer. In another example, a powder resin can be applied with an electrostatic gun, whereby the powder is blown over a negatively charged electrode as it is discharged from the gun in the form of a cloud of charged particles. The charged particles are attracted to the surface of the substrate, and the powder is cured with heat.

Another suitable coating method employs powder from a fluidized bed that is formed when a stream of air is directed into a container filled with the powder. The powder is subsequently electrostatically charged before a grounded metal substrate is dipped into the fluidized bed. The substrate is removed and the powder is cured with heat.

When employing the electrostatic spray technique, the material for use in the coating process can comprise any material that can be electrically charged and which will adhered to the substrate surface. The material used is in powder form and will typically have an average size that ranges from 10 μm to 250 μm, preferably from 20 μm to 150 μm. It is expected that smaller sized particles will provide for more even coating.

The electrostatic spray or fluidized bed technique can also be employed to form the echogenic layer when it includes glass microspheres or void forming particles. This can be accomplished by forming successive layers of polymeric material onto the substrate surface; glass microspheres are attached to a first layer prior to the formation of the next layer. In this fashion, the microspheres become embedded in the polymer matrix.

Another technique to form the echogenic layer involves forming a mixture containing the polymeric material and glass microspheres and then electrostatically applying the mixture to form a layer on the surface of the substrate. The layer is "cured" with heating.

It has been demonstrated that an echogenic layer comprising glass microspheres and NYLON 11 in a weight ratio of 1:4 that is coated on a stainless steel substrate provides excellent ultrasound signals.

A preferred method of forming the echogenic layer that comprises void space is to formulate a mixture comprising a polymer material and a soluble agent. By "soluble agent" is meant a suitable material including, for example, a salt or hydrocarbon that is substantially or essentially completely soluble in a selected solvent or mixture of solvents with the proviso that the same solvent or mixture of solvents does not substantially or essentially completely dissolve the polymer material. That is, the soluble agent has a higher solubility in the solvent than does the polymer material. In this fashion, when the mixture comprising the polymer material and the soluble agent is exposed to the selected solvent or mixture of solvents the soluble agent is dissolved thereby leaving an echogenic layer that contains void spaces that are created by the dissolution (or extraction) of the soluble agent.

In one preferred embodiment, polymer material is mixed with water soluble salt such as NaCl, KCl and soluble nitrate, phosphate, and sulfate salts, for example, of sodium or potassium. The polymer material can comprise polymer precursors which require curing in which case the mixture is cured (e.g, heated) and then immersed in water to extract the salt. The result is a echogenic layer having void spaces dispersed therein. It was demonstrated that mixtures of NaCl and NYLON 11 where the salt to NYLON weight ratio was from about 1:1 to 1:10 provided an enhanced ultrasound signal. Preferred ratios of 1:3 or 1:5 gave an enhanced signal and provided a smooth echogenic surface.

Alternately, the soluble agent can be a hydrocarbon with higher solubility in the solvent than does the polymer matrix material. Suitable hydrocarbons include, for example polyvinyl chloride, ABS resins, styrene, urethane, and polycarbonate. When such hydrocarbons are employed suitable solvents include, for example, ketones, aromatic hydrocarbons, aliphatic hydrocarbons, methyl ethyl ketone, toluene, hexane and methylene chloride.

The echogenic coating of the present invention can be employed with any medical device used with an ultrasound imaging system especially devices that are exposed to high voltage electrical energy. The echogenic coating affords electrical insulation to devices used for RF electrosurgical procedures. It has been demonstrated that elongated instruments that are coated with the inventive echogenic coating produce enhanced ultrasound reflection even when viewed along their length.

The echogenic coating is particularly suited for coating devices that are employed to treat uterine disorders, particularly uterine fibroids, by occluding the uterine arteries using trans-vaginal, trans-uterine, trans-rectal, and retroperitoneal approaches. These devices are described in U.S. patent application Ser. No. 09/207,572 filed on Dec. 8, 1998, which is incorporated herein by reference. Exemplary devices coated with the echogenic coating are further described herein.

One exemplary device for treating disorders which receive blood from the uterine arteries by causing at least partial occlusion of a uterine artery comprises means for sensing a location of a uterine artery; and means for at least partially penetrating an anatomical structure in the region of the uterine artery to cause at least partial occlusion of the uterine artery to thereby decrease the blood flow to the uterus and said disorder.

A second exemplary device for treating disorders in a human female, which receive blood from at least one of the uterine arteries, by causing at least partial occlusion of a uterine artery comprises a cannula having a proximal end and a distal end, an ultrasonic transducer positioned adjacent said distal end, said ultrasonic transducer capable of sensing the location of anatomical structures in a sensing plane when energized, and a tissue penetrating member having a distal end and being movable relative to said cannula between a retracted position and a extended position, said tissue penetrating member distal end being substantially in said sensing plane when said tissue penetrating member is in said extended position.

A third exemplary device is a system for treating disorders in a human female, which receive blood from at least one of the uterine arteries, by effecting at least partial occlusion of a uterine artery comprises a locating cannula having a proximal end and a distal end, said locating cannula including a locating device positioned adjacent said distal end, said locating device capable of sensing the location of anatomical structures in at least a sensing plane when energized, and a tissue penetrating cannula having a distal end and including a tissue penetrating member, said tissue penetrating cannula being movable independent from and relative to said locating cannula between a retracted position and a extended position, said tissue penetrating member distal end being substantially in said sensing plane when said tissue penetrating member is in said extended position.

FIG. 2 illustrates an intrauterine instrument 30 constructed to enable a practitioner to readily occlude the uterine arteries. Instrument 30 includes a proximal handle 38 and a cannula 36. Cannula 36 includes a rigid shaft 40 and a distal portion 42. Cannula 36 preferably includes a first lumen 44 (see FIG. 6) which extends from the proximal end of instrument 30 to a distal port 45. A guidewire 46 is positioned in lumen 44 and is movable out distal port 45 and sufficiently rigid to guide cannula 36 into the uterus of a patient, yet flexible enough to conform to the shape of a uterus without damaging it.

A supporting member 58 is positioned in distal portion 42, and extends or is extendable away from cannula 36 to push against a uterine wall, deflect distal portion 42 toward an opposite uterine wall, and support the cannula in the uterine cavity, as described in greater detail below. Distal portion 42 of cannula 36 also includes an imaging window 54 on a side of the cannula opposite supporting member 58, so that when the supporting member bears against a uterine wall, the window is pressed up against an opposite uterine wall.

As illustrated in FIG. 2, supporting member 58 includes a band or belt 55 which is laterally flexible, to allow the belt to be flexed in and out, yet longitudinally rigid, so the supporting member does not collapse. Suitable materials for belt 55 include some stainless steels, nickel/titanium alloys, polymers, composite materials, and other materials which will be readily apparent to one of ordinary skill in the art. The distal end 57 of belt 55 is preferably attached to cannula 36. The proximal end of belt 55 (not illustrated) is preferably longitudinally movable to flex or bow the belt in and out to bear against a uterine wall, causing cannula 36 to move toward the opposite uterine wall. According to an alternate embodiment, the proximal end of belt 55 can also be immovably attached to cannula 36, with a middle section which protrudes away from cannula 36 as illustrated in FIG. 2. In this alternate embodiment, belt 55 presses against a uterine wall a predetermined amount when inserted into a uterine cavity.

Cannula 36 is further provided with a tissue, preferably uterine tissue, penetrating member 52, which extends distally through rigid shaft 40 from a proximal port 60 to a distal guide port 63 in distal portion 42. Member 52 is guided by and extendable out of guide port 63 so that a distal end 53 of the tissue penetrating member is substantially in the same plane as an imaging, viewing, or sensing plane of a locating device carried by instrument 30, described in greater detail below. Guide port 63 guide member 52 so that distal end 53 remains in this plane (see FIG. 5), so that procedures which are performed by means of the tissue penetrating member can be viewed by the practitioner without the need for aligning a viewing device and the tissue penetrating member. Preferably, guide member 52 and distal end 53 are coated with the inventive echogenic material comprising an electrically insulative base layer and an echogenic layer.

Member 52 includes a device on distal end 53 which allows the member to penetrate the muscular uterine wall tissue. In accordance with a first embodiment of the present invention, this penetrating device is a hollow needle including a bore large enough to pass instruments therethrough. In accordance with a second embodiment of the present invention, penetrating device includes an RF energy cutting element and an RF energy conducting wire extending from the cutting element proximally through instrument 30 to an RF generator (not illustrated). RF energy is preferably utilized in the present invention for penetrating the uterine wall, because it cauterizes as it cuts through tissue, resulting in substantially less bleeding. Furthermore, RF energy cutting very efficiently cuts tissue, resulting in relatively effortless advancement of tissue penetrating member 52 into and through the uterine wall toward the uterine artery.

The junction 41 between rigid shaft 40 and distal portion 42 can be either rigid or flexible, and if rigid, either straight or angled. Preferably, junction 41 is flexible so that distal portion 42 can be deflected to one side of longitudinal axis 56 by supporting member 58, as described above. Optionally, instrument 30 can include a pullwire system, described in greater detail below with reference to FIGS. 3 and 4, which operates in conjunction with or in place of supporting member 58 to deflect distal portion 42. Less preferably, junction 41 can be rigid. Distal portion 42 can be rigidly attached to rigid shaft 40 at a predetermined angle (not illustrated) which would allow the practitioner to insert instrument into a uterine cavity and easily press viewing window 54 against a uterine wall, while supporting member 58 maintains this orientation. Even less preferable, junction 41 can be rigid and straight.

Turning now to FIGS. 3 and 4, yet another embodiment of instrument 30 is schematically illustrated. In this embodiment, junction 41 is flexible so that distal portion 42 can be flexed from a straight orientation (FIG. 3) to a flexed orientation (FIG. 4), for the reasons stated above. FIGS. 3 and 4 also illustrate a pullwire system 100 which assists in flexing or bending cannula 36 at junction 41, in addition to or instead of supporting member 58, and holding the cannula in this orientation. Pullwire system 100 includes a longitudinally rigid wire 102 extending from a distal end 104 which is rigidly attached to cannula 36 in distal portion 42, and a proximal end 106 which is attached to a pullwire handle 108. Handle 108 is slidably received in handle 38, and pullwire 102 is slidably received in a lumen 110 which extends parallel to tissue penetrating member 52. Handle 108 includes a set of teeth 112 against which a detent 114 is forced by a spring 116. The combination of spring 116, detent 114, and teeth 112 result in handle 108 being held in discrete, particular longitudinal positions. As will be readily appreciated by one of ordinary skill in the art, pulling proximally on handle 108 results in pullwire 102 deflecting distal portion to the right in FIGS. 3 and 4, which position is maintained without further user action by detent 114 acting on teeth 116.

FIGS. 5 and 6 illustrate cannula 36 being used to visualize, provide an image of, or otherwise sense the position and location of a uterine artery 20. A locating device 70 is mounted in distal portion 42. Locating device 70 can be an ultrasonic imaging device, a gray scale color 2D (Duplex) Doppler ultrasound system, available, for example, from Diasonics, of Santa Clara, Calif., Doppler audio ultrasound systems or other locating systems which are generally available to and used in gynecological practice, including other conventional ultrasound systems as will be readily apparent to one of ordinary skill in the art. Locating device can be a combination of systems, e.g., a 2D (Duplex) Doppler ultrasound system with a Doppler audio ultrasound system, a less complicated, single system, e.g., Doppler audio ultrasound system alone, or even a simple landmarking system, e.g., markings on the outer wall of the cannula so a practitioner can visually determine the location of the cannula relative to anatomical features of the patient. A Doppler audio ultrasound system can advantageously be used by the practitioner listening for an increase in the magnitude of sound produced by the system, which indicates an increase in blood flow velocity near the focal point of the system. Additional details of such Doppler audio ultrasound systems will be readily apparent to one of ordinary skill in the art.

In the embodiment illustrated in FIG. 5, ultrasound imaging device 70 generates an image in a plane or portion of a plane 68, which is pointed or directed through viewing window 54. As discussed above, tissue penetrating member 52 is extendable into and along this plane 68, so that distal tip 53 (not illustrated in FIG. 8 for ease of visualization) of member 52 can be visualized by device 70 while penetrating the uterine wall toward uterine artery 20. The alignment of the sensing or viewing plane of device 70 and tissue penetrating member 52 allows the gynecologist to easily find and occlude the uterine artery with instruments and processes in accordance with the present invention.

FIG. 6 illustrates a cross-sectional view of cannula 36, taken at line 5—5 in FIG. 5. A lumen 44 is illustrated through which guidewire 46 (not illustrated in FIGS. 5 and 6) extends, a lumen 48 in which viewing device 70 is mounted, and a lumen 50 through the proximal portions of which tissue penetration member 52 extends.

FIG. 7 illustrates another device. A cannula 136 includes a rigid shaft 140 to which a handle 138 is attached. Cannula 136 does not include a flexible portion, but may optionally include a bent distal portion 142. A viewing window 154 is provided at the distal end of cannula 136, directed distally. Similarly, a tissue penetrating member 152 is provided which is extendable distally from the distal end of cannula 136. Member 152 is preferably coated with the inventive echogenic material. Similar to the embodiments previously described, tissue penetrating member 152 is extendable into and along the plane of an imaging device (not illustrated in FIG. 7) which is mounted in the distal end of cannula 136, and which directs its viewing plane distally of the cannula distal end.

FIGS. 8–13 illustrate numerous exemplary embodiments of devices for at least partially, and optionally completely occluding a uterine artery. The embodiments illustrated in FIGS. 8–13 preferably share at least one common characteristic: they are each extendable through or with tissue penetrating member 52 or 152 through the uterine or vaginal wall of a patient to the uterine artery of interest. For this purpose, tissue penetrating member 52 or 152 which are coated with the echogenic material further includes a lumen 59 extending between a proximal end 61 and distal end 53, which allows a practitioner to push one of the devices through the tissue penetrating member which are coated with the echogenic material 52 or 152 to effect occlusion of a uterine artery.

Turning now to the individual drawing figures, FIG. 8 illustrates a snare 160 which is sized to pass through lumen 59. Snare 160 includes a tubular shaft 162 which is resiliently flexible to allow the snare to be extended through lumen lumen 59, and rigid enough to avoid kinking. Snare 160 includes two interlocking fingers 164, 166 which extend out of shaft 162 and include interlocking portions 168, 170 at their respective distal end. The shaft 162 and fingers 164 and 166 are preferably coated with the inventive echogenic coating. The proximal ends of fingers 164, 166 (not illustrated) are hinged together, and are attached to a longitudinally extending actuating rod 172. Fingers 164, 166 are biased away from each other by their own resilience, so that interlocking portions 168, 170 open to allow snare 160 to be advanced over a uterine artery.

To use snare 160 to occlude a uterine artery, shaft 162 is advanced out the distal end 53, 153 of tissue penetrating member 52, 152 after the member has penetrated the uterine wall and is adjacent the uterine artery of interest. Imaging device 70 allows a practitioner to accurately position distal end 53, 153 adjacent the uterine artery. Rod 172 is then pushed, allowing fingers 164, 166 to separate. The snare is then advanced over the uterine artery and adjacent tissues, and rod 172 is pulled back. Snare 160 is sized so that when interlocking portions 168, 170 meet, snare 160 crushes the uterine artery, and immediately adjacent tissues if necessary or convenient, thus forming an occlusion. These steps are then reversed for removing snare 160, leaving the uterine artery crushed and occluded.

FIG. 9 illustrates a clamp or staple applier 192 which can be used in a fashion similar to snare 160. Clamp 192 includes two jaws 194, 196 which are biased apart and are hinged to an actuating rod 198. The actuating rod 198 and jaws 194, 196 are coated with the inventive echogenic material except that the inner surfaces of the jaws that are facing each other are not. The use of clamp 192 to occlude a uterine artery is somewhat similar to the use of snare 160, except that jaws 194, 196 are forced closed by distal end 53,153 of tissue penetrating member 52, 152, in a manner similar to shaft 162. Jaws 194, 196 are advanced out of distal end 53, 153 and around a uterine artery of interest. Tissue penetrating member 52, 152 is then further distally advanced to bear on the outer portions of jaws 194, 196, forcing the jaws toward each other to crush the uterine artery between them. When used as a staple applier 192, jaws 194, 196 include an anvil (not illustrated) therebetween for a staple to be deformed against.

Another example of incorporating multiple mechanisms of occlusion of a uterine artery is to form actuating rod 198 and jaws 194, 196 of a material which allows the jaws to function as a heater to close, seal, or otherwise occlude the uterine artery and adjacent tissue caught between them. By connecting rod 198 to an appropriate electric source, and forming jaws 194, 196 of a resistive heating material, the partially or completely crushed uterine artery can be further occluded by heating the vessel tissues, blood, or both sufficiently to cause an embolism to form in the uterine artery. As will be readily appreciated by one of ordinary skill in the art, combining two or more mechanisms of occlusion in accordance with the principles of the present invention allows a practitioner to more confidently occlude a uterine artery, because the plurality of mechanisms provides a redundancy of occlusion modalities which greatly increases the success rate of vessel occlusion.

FIG. 10 illustrates an RF energy probe 200 including an RF energy tip 202 and a conducting rod 204 which is preferably coated with the inventive echogenic material. Conducting rod 204 is in electrical communication with an RF energy generator (not illustrated) proximal of handle 38, 138. In a manner which will be readily appreciated by one of ordinary skill in the art, probe 200 can be advanced out distal end 53, 153 of tissue penetrating member 52, 152 to a point adjacent a uterine artery. RF energy is then allowed to flow through conducting rod 204 to tip 202, to heat the uterine artery, adjacent tissues, and blood in the uterine artery to cause the uterine artery to be occluded. In another embodiment, probe 200 can used instead of tissue penetrating member 52, 152, and operated at different power levels: a high power level to advance through the uterine wall; and a lower energy lever to heat the uterine artery, blood in the uterine artery, or both to cause occlusion.

FIG. 11 illustrates a microwave probe 206 including a microwave antenna 208 housed within a protecting sleeve 210 which is preferably coated with the inventive echogenic material. In a manner similar to probe 200, probe 206 can be advanced to a point adjacent a uterine artery of interest, and microwave energy can be emitted from antenna 208 to heat the uterine artery, adjacent tissues, and blood in the uterine artery to cause the uterine artery to be occluded.

FIGS. 11a–11c illustrate a probe 165 which includes a tubular member 167 and a wire 169. The tubular member is preferably coated with the echogenic material. Wire 169 is movable longitudinally relative to probe 165 to advance the wire distally of the distal end of the probe. Wire 169 is formed of a material which has "memory," i.e., will change shape from a first shape to a second shape when a particular stimulus affects the wire. Preferably, wire 169 is formed of a shape memory alloy (SMA) which has been formed to have a first, straight shape, illustrated in FIG. 11a, and a second, curved shaped, illustrated in FIG. 17c. More preferably, wire 169 is formed of a shape memory alloy having a transition temperature between about 65° F. (18.3° C.) and about 100° F. (37.8° C.), so that the wire has an open configuration below the transition temperature and a closed configuration above the transition temperature. The details of SMAs and their uses will be understood by one of ordinary skill in the art.

In order to use probe 165 to occlude a uterine artery 20 of interest, probe 165 is maintained at a temperature below its transition temperature, and therefor wire 169 remains in its first, straight shape. It is then advanced through tissue penetrating member 52, 152 to a point adjacent to a uterine artery in a manner so that its temperature remains below the SMAs transition temperature. Wire 169 then heats up because of its intimate contact with tissue, and continues to heat up to reach a steady state temperature near that of the tissue in which it is inserted. As wire 169 heats up to a temperature above the transition temperature of the SMA of which it is formed, the wire begins to change shape toward its second, curved shape, illustrated in FIG. 11b. As wire 169 changes shape as it heats up, the wire loops around uterine artery 20. As wire 169 reaches a temperature close to the temperature of the tissue in which it has been inserted, the wire has completed the transition to its second, curved shape and has snared uterine artery 20 (see FIG. 11c). At this point, wire 169 can be pulled back to crush the uterine artery, and immediately adjacent tissues if necessary or convenient, thus forming an occlusion. Thereafter, wire 169 can be detached from probe 167 and left around uterine artery 20. Alternatively, wire 169 can be cooled by injection of cold fluid, e.g. saline, down tubular member 167 to cause the wire to straighten, because the wire's temperature is dropped below the SMA transition temperature, as will be readily appreciated by one of ordinary skill in the art. When wire 169 is straight, it can then be withdrawn.

FIGS. 12–13 illustrate a probe 214 which can be used to position a loop or suture 212 around a uterine artery 20 and cinched closed to crush the uterine artery (FIG. 13). Probe 214, which is preferably coated with the inventive echogenic material, includes two tubular members 215, 217 which are movable both proximally and distally relative to a tube 219, but also can pivot toward and away from each other in a manner which will be readily apparent to one of ordinary skill in the art. Tubular member 215 includes a first guide tube 221 and a second guide tube 223 connected to first guide tube 221 at an angle. Second guide tube 223 extends toward and is open toward tubular member 217, and preferably includes a sharpened end 225. First guide tube 221 preferably includes a barrier 227 inside lumen 229, to guide suture 212 into second guide tube 223. Tubular member 217 includes a lumen 231 which opens at a port 233. Preferably, tubular member 217 includes a barrier 235 to guide suture 212 proximally down lumen 231.

To use probe 214 to occlude a uterine artery, the probe is advanced out of a tissue penetrating member 52, 152 so that tubular members 215, 217 are positioned on opposite sides of a uterine artery 20 of interest (see FIG. 12b). Suture material 212 is loaded into lumen 229, preferably by advancing the suture material distally, as indicated by arrow 237. Tubular member 215, 217 are then pivoted toward each other to that sharpened end 225 of second guide tube 223 moves through tissue around uterine artery 20 and seats itself in port 233 of tubular member 217 (see FIG. 12a). A length of suture material 212 is then pushed out of second guide tube 223 in the direction indicated by arrow 239, through port 233, and into lumen 231. Barrier 235 guides suture 212 proximally along lumen 231, in the direction indicated by arrow 241. Then, tubular members 215, 217 are pivoted away from each other and withdrawn into tube 219, leaving a loop of suture material around uterine artery 20 (see FIG. 12). Loop 212 can be either left around uterine artery 20, or released after a predetermined length of time sufficient to ensure that the uterine artery is occluded. If loop 212 is left in place, cinched around artery 20 (see FIG. 13), loop 212 may optionally be formed of a resorbable material which slowly dissolves over time.

Although only preferred embodiments of the invention are specifically disclosed and described above, it will be appreciated that many modifications and variations of the present invention are possible in light of the above teachings and within the purview of the appended claims without departing from the spirit and intended scope of the invention.

What is claimed is:

1. An echogenic material comprising:
   an electrically insulative base layer that has a thickness of at least about 100 μm and
   an echogenic layer that comprises a polymeric matrix that (i) defines a plurality of void spaces, (ii) includes glass microsphere particles, or (iii) both defines a plurality of void spaces and includes glass microsphere particles, wherein the echogenic layer is formed on the base layer.

2. The echogenic material of claim 1 wherein the electrically insulative base layer comprises a thermoplastic material or a thermoset material.

3. The echogenic material of claim 2 wherein the electrically insulative base layer comprises a thermoplastic material that is selected from the group consisting of polyamide, polyolefin, polytetrafluoroethylene, polyester, and mixtures thereof.

4. The echogenic material of claim 3 wherein the thermoplastic material is nylon.

5. The echogenic material of claim 2 wherein the electrically insulative base layer comprises epoxy.

6. The echogenic material of claim 1 wherein the echogenic layer includes glass microspheres having an outer diameter of about 10 μm to 100 μm.

7. The echogenic material of claim 1 wherein the echogenic layer defines void spaces or includes microspheres that collectively occupy about 10% to 50% by volume of the echogenic layer.

8. The echogenic material of claim 1 wherein the electrically insulative base layer has a thickness of from about 100 μm to 300 μm.

9. The echogenic material of claim 1 wherein the echogenic layer has a thickness of from about 20 μm to 200 μm.

10. A process for forming an echogenic layer on a substrate surface that comprises the steps of:
    (a) applying an electrically insulative base layer on the substrate surface that has a thickness of at least about 100 μm; and
    (b) creating an echogenic layer on the insulative base layer wherein the echogenic layer comprises a polymeric matrix that (i) defines a plurality of void spaces, (ii) includes glass microsphere particles, or (iii) both defines a plurality of void spaces and includes glass microsphere particles, wherein the echogenic layer has a thickness of at least about 20 μm is formed on the base layer.

11. The process of claim 10 wherein step (a) comprises generating electrostatically charged particles of polymer material and allowing the charged particles to adhere to the substrate surface.

12. The process of claim 10 wherein step (a) comprises the steps of:

(i) generating a gaseous stream containing particles of polymer material; and (ii) contacting the substrate surface with the particles of polymer material and allowing the particles to adhere to the substrate surface.

13. The process of claim 10 wherein the echogenic layer comprises a polymeric matrix that defines a plurality of void spaces and the polymer matrix is formed by the steps of:

(i) providing a mixture comprises a polymer matrix and a soluble agent;

(ii) curing the polymeric matrix with heat; and (iii) exposing the mixture to a liquid to solubilize and remove the soluble agent from the mixture thereby forming the polymeric matrix with the plurality of void spaces.

14. The process of claim 10 wherein the soluble agent is water soluble salt and step (ii) comprises exposing the mixture to water.

15. The process of claim 14 wherein the salt is selected from the group consisting of NaCl, KCl, nitrate salts, phosphate salts and sulfate salts and mixtures thereof.

16. The process of claim 10 wherein the soluble agent is a hydrocarbon.

17. The process of claim 16 wherein the hydrocarbon is selected from the group consisting of polyvinyl chloride, ABS resins, stryrene, urethane, and polycarbonate, and mixtures thereof and step (ii) comprises exposing them mixture to an organic solvent that is selected from the group consisting of ketones, aromatic hydrocarbons, aliphatic hydrocarbons, halogenated hydrocarbons, methyl ethyl ketone, toluene, hexane, methylene chloride, and mixture thereof.

18. The process of claim 10 wherein echogenic layer comprises glass microspheres that are embedded in the polymer matrix.

19. A system for applying RF energy to tissue that comprises:

an ultrasonic transducer means for sensing a location in the tissue to be treated;

means for applying RF energy that includes an RF probe having a distal end and an RF electrode mounted on the distal end wherein the RF probe has a surface that has an echogenic material coated thereon which comprises an electrically insulative base layer that is deposited on the surface of the RF probe and that has a thickness of at least about 100 µm and an echogenic layer that is deposited on a surface of the electrically insulative base layer.

20. The system of claim 19 wherein the echogenic layer that comprises a polymeric matrix that (i) defines a plurality of void spaces, (ii) includes glass microsphere particles, or (iii) both defines a plurality of void spaces and includes glass microsphere particles.

21. The system of claim 20 wherein the echogenic layer has a thickness of from 20 µm to 200 µm.

22. The system of claim 19 wherein the second layer comprises an electrically insulative coating comprises material that is selected from the group consisting of polyamide, polyolefin, polytetrafluoroethylene, polyester, and mixtures thereof.

23. The system of claim 22 wherein the electrically insulative layer has a thickness of from 100 µm to 300 µm.

24. The system of claim 19 wherein the ultrasonic transducer means comprises a two-dimensional ultrasonic transducer.

25. The system of claim 24 wherein the system further comprises a Doppler imaging device.

26. The system of claim 24 wherein the ultrasonic transducer senses a location of an artery by Doppler imaging.

27. The system of claim 26 wherein the means for applying RF energy includes means for at least partially penetrating an anatomical structure in a region of the artery to cause at least partial occlusion of the uterine artery to thereby decease the blood flow to the uterus.

28. A medical device for insertion into biological tissue said device having a metal substrate and having an echogenic portion of enhanced visibility in an ultrasound scan, wherein the echogenic portion comprises a coating comprising an electrically insulative layer that is deposited on a surface of the metal substrate and an echogenic layer that is deposited on a surface of the electrically insulative layer.

29. A medical device for insertion into biological tissue having a shaft member and a source of RF energy wherein the shaft member has an outer surface that is coated with a coating comprising an electrically insulative layer that is deposited on a surface of the shaft member and an echogenic layer that is deposited on a surface of the electrically insulative layer.

30. The medical device of claim 29 wherein the echogenic layer comprises a polymeric matrix that (i) defines a plurality of void spaces, (ii) includes glass microsphere particles, or (iii) both defines a plurality of void spaces and includes glass microsphere particles.

31. A method for sonically imaging an echogenic medical device in biological tissue, comprising:

selecting a medical device that includes:

(i) an ultrasonic transducer means for sensing a location in the tissue to be treated; and (ii) means for applying RF energy that includes a shaft member having a distal end and an RF electrode mounted on the shaft member distal end wherein the shaft member has an echogenic material coated thereon which comprises an electrically insulative base layer that is deposited on a surface of the shaft member and an echogenic layer that is deposited on a surface of the electrically insulative base layer;

inserting the shaft member into the tissue;

directing a sonic beam towards the shaft member;

receiving an image of the shaft member;

maneuvering the RF electrode to the location in the tissue to be treated; and applying RF energy to the tissue.

32. A method for manufacturing an echogenic medical device for insertion into biological tissue and imageable with sonic imaging equipment, comprising:

providing a medical device that includes means for applying RF energy that includes a shaft member having a distal end and an RF electrode mounted on the shaft member distal end; and applying an echogenic coating on the shaft member wherein the echnogenic coating comprises an electrically insulative base layer and an echogenic layer.

* * * * *